United States Patent [19]

Choksi et al.

[11] 4,210,173
[45] Jul. 1, 1980

[54] SYRINGE PUMPING SYSTEM WITH VALVES

[75] Inventors: Pradip V. Choksi, Northridge; Donald L. Johnston, Arcadia, both of Calif.

[73] Assignee: American Hospital Supply Corporation, Evanston, Ill.

[21] Appl. No.: 940,060

[22] Filed: Sep. 6, 1978

Related U.S. Application Data

[63] Continuation of Ser. No. 747,415, Dec. 6, 1976, abandoned.

[51] Int. Cl.² ............................................. F16K 15/14
[52] U.S. Cl. ............................ 137/512.3; 137/843; 137/854; 128/273; 128/274
[58] Field of Search ............... 137/512, 512.3, 843, 137/854; 128/273, 274, 278, 214 B; 417/566

[56] References Cited

U.S. PATENT DOCUMENTS

| 1,976,098 | 10/1934 | Smith | 417/566 |
|---|---|---|---|
| 2,710,004 | 6/1955 | Stamper | 128/214 |
| 3,132,665 | 5/1964 | Rovin et al. | 137/512 |
| 3,373,743 | 3/1968 | Saffir | 128/218 |
| 3,386,470 | 6/1968 | Goda et al. | 137/512 |
| 3,447,479 | 6/1969 | Rosenberg | 417/271 |
| 3,572,375 | 3/1971 | Rosenberg | 137/512 |
| 3,626,978 | 12/1971 | Hoekstra | 137/854 |
| 3,633,613 | 1/1972 | Jolow | 137/512.3 |
| 3,643,686 | 2/1972 | Koegel | 137/512 |
| 3,650,093 | 3/1972 | Rosenberg | 55/159 |
| 3,661,174 | 5/1972 | Cripe | 137/854 |
| 3,727,614 | 4/1973 | Kniazuk | 128/218 A |
| 3,807,445 | 4/1974 | McPhee | 137/557 |
| 3,905,386 | 9/1975 | Rachocki | 137/215 |
| 3,949,934 | 4/1976 | Goglio | 137/843 X |
| 3,954,121 | 5/1976 | Kardos | 137/854 |
| 3,957,052 | 5/1976 | Topham | 128/278 |
| 4,051,852 | 10/1977 | Villari | 137/512.3 |
| 4,084,606 | 4/1978 | Mittleman | 137/102 |

Primary Examiner—William R. Cline
Attorney, Agent, or Firm—Larry N. Barger

[57] ABSTRACT

A pumping system with inlet and outlet check valves for delivering measured doses of liquid from a reservoir container, which might include sterile normal saline solution, to a series of smaller vials or hypodermic syringes. This pumping system has an improved valve system that includes a heavily biased check valve and a lightly biased check valve. An embodiment of the system has a valve body with an inlet passage surrounded by a valve seat, and an outlet valve member is biased against this valve seat by a pressure that is substantially greater than a pressure biasing an inlet check valve against its valve seat. A heavy bias at only one valve both (1) prevents valve leakage from the system due to a liquid pressure head from the reservoir container and (2) reduces operator fatigue.

7 Claims, 4 Drawing Figures

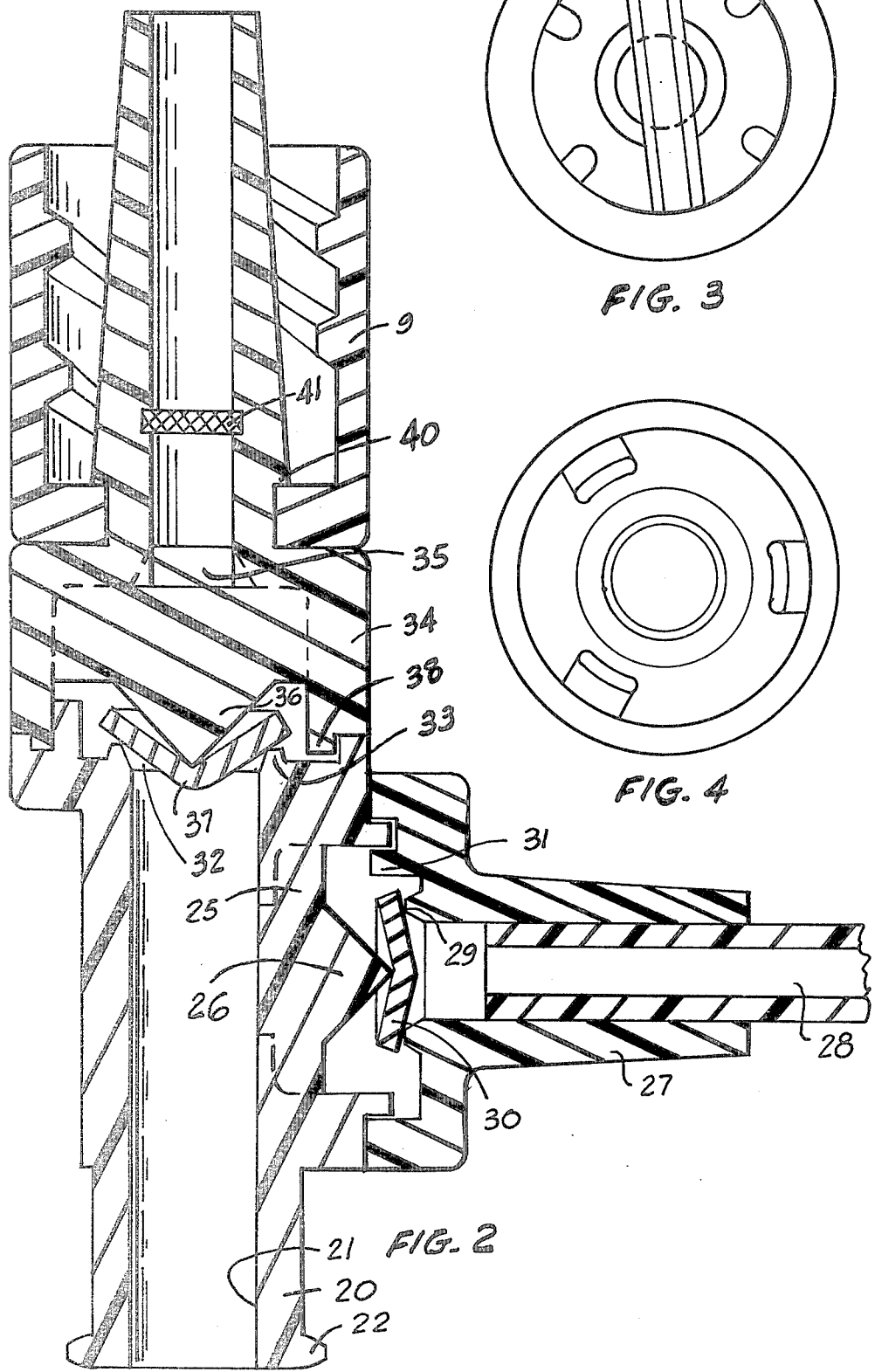

ying of application Ser. No. 747,415
SYRINGE PUMPING SYSTEM WITH VALVES

This is a continuation of application Ser. No. 747,415 filed Dec. 6, 1976, now abandoned.

BACKGROUND OF THE INVENTION

In hospitals hypodermic syringes and small vials are frequently partially filled with a medicament. The concentration of the medicament is then altered by injecting a measured volume of a diluent, such as sterile water or normal saline. These diluents, and sometimes the medicaments themselves, are supplied to the hospital pharmacy in large bulk containers.

In the past, the pharmacists had used a syringe pumping system with two check valves to pump a measured dose of diluent or medicament to a series of hypodermic syringes or vials. Such syringes or vials could then be transferred from the pharmacy to the hospital floors for injection into patients.

A problem with these syringe pumping systems involved the check valve system. Because the reservoir was hung mouth downwardly from a height of 2-3 feet above the check valve to insure proper drainage, a pressure head in this amount was created at the check valves. To prevent leakage at the check valves, one system proposed using very strong coil springs to provide a very strong closing force at both the inlet and outlet check valves. If a spring were provided to assist on a rearward filling stroke of a metering syringe to overcome the high bias of the inlet check valve, a forward stroke of the metering syringe had to overcome this large spring force as well as the heavily biased outlet valve. Numerous manual strokes of the metering syringe to overcome this large resistance could cause operator fatigue.

To overcome the operator fatigue problem it has been suggested to use weakly biased duckbill valves as the inlet and outlet check valves. To overcome a leakage problem through such weakly biased duckbill valves, it was proposed to place a small piece of foam material wedged across the openable slot of the inlet duckbill valve. A duckbill valve has two rubber members that open and close against itself somewhat like the action of a duck's bill. A duckbill valve does not require engagement and disengagement from a seat on a rigid valve body.

It would appear that the small piece of foam material wedged against the openable slot of the duckbill valve could readily get wedged into such slot holding it continuously open. To our knowledge, the double duckbill valve system has never been marketed with the small piece of foam material across the inlet duckbill valve.

SUMMARY OF THE INVENTION

The present invention overcomes the above problems of operator fatigue and leakage through the inlet and outlet check valves due to head pressure from the reservoir bottle. One of the check valves is heavily biased against its valve seat while the other check valve is lightly biased against its seat. In a preferred embodiment of this invention an inlet valve member is lightly biased against its valved seat while the outlet valve is heavily biased against its valve seat so that a substantially greater opening pressure is required at the outlet check valve than at the inlet check valve. Both the inlet and outlet check valves are preferably flexible resilient disks urged against their respective valve seats by central pressure posts. A greater biasing is accomplished by the outlet check valve post than is by the inlet check valve post.

In use, a compression coil spring on an attached metering syringe retracts the metering syringe's plunger creating a vacuum within the metering syringe that opens the inlet check valve. Because the inlet valve bias is light this retracting spring can be light. If the combined lightly biased inlet valve and metering syringe plunger sliding resistance are less than the liquid head, the metering spring will fill automatically and no retracting spring is needed. After the metering syringe is filled with its proper dosage, the inlet check valve closes. The heavily biased outlet check valve prevents leakage from the valve structure. A pharmacist can discharge the dose from the metering syringe by a simple forward plunger stroke to overcome the weak retracting spring force and the outlet valve resistance.

While it is preferred to have the heavily biased valve only at the outlet, the heavily biased valve could be only at the inlet and not materially affect the force required on a forward stroke of the metering syringe. This is because a heavy resistance force at the outlet valve would be replaced with the resistance of a larger retracting spring to overcome the heavily biased inlet valve.

BRIEF DESCRIPTION OF THE DRAWINGS

FIG. 2 is an enlarged sectional view showing the details of the inlet check valve and the outlet check valve structure;

FIG. 3 is a sectional view taken along line 3—3 of FIG. 2; and

FIG. 4 is a sectional view taken along line 4—4 of FIG. 2.

DETAILED DESCRIPTION

Figure 1:
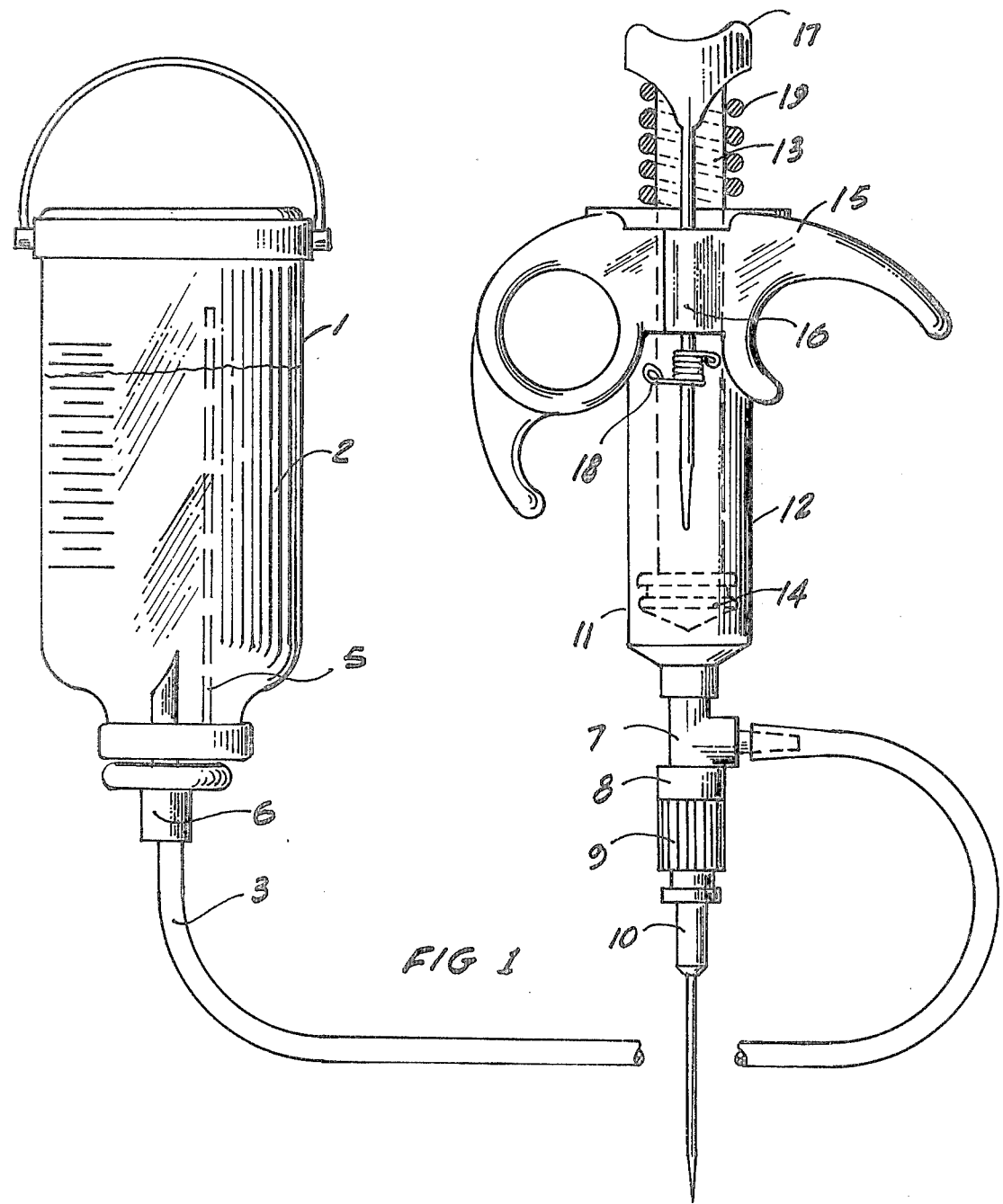
FIG. 1 is a front elevational view of the syringe pumping system with valves showing it connected to a liquid reservoir container.

FIG. 1 shows a reservoir bottle 1 containing a diluent liquid 2, such as sterile water or normal saline. This reservoir bottle 1 is hung 2-3 feet above the metering syringe and attached valve to insure proper drainage of the diluent liquid 2 through a flexible tube 3 to valve 4.

As liquid drains through flexible tube 3 air is replaced in bottle 1 through air tube 5. If desired, air tube 5 could be eliminated and a rigid tubular spike 6 replaced with an air inletting spike. Such an air inletting spike could include an air passage closed off by a check valve permitting air to enter the reservoir container 1, but prevent liquid from draining out the air inlet passage. A filter member could also be provided across the air inlet passage. If desired, the reservoir container could be supported on a table with an opening in its top. Then a flexible tube connecting the reservoir to the valve could have a hollow weighted ball to hold an inlet of the flexible tube below the reservoir's liquid level.

The valve 4 shown in FIG. 1 includes an inlet check valve section 7 and an outlet check valve section 8. At a forward end of the valve is a rotatable internally threaded collar 9 for attaching to a hypodermic needle 10, a flexible tubing adapter, or a special adapter to convert the forward end of the valve to receive syringes with internally threaded collars at their forward end.

Connected to a rear of the valve 4 is a metering syringe 11, which includes a barrel 12 and a plunger 13 with a resilient stopper 14 connected to its forward end.

At a rear of the syringe barrel is a handle structure 15 with a guide channel 16. A dose setting member 17 has an adjustable spring member 18. Compression coil spring 19 urges the plunger and dose measuring device 17 rearwardly from barrel 12. The details of the handle, and dose measuring structure is described in detail in a copending patent application invented by William G. Bloom et al, filed Dec. 6, 1976, Ser. No. 747,417, now U.S. Pat. No. 4,098,276.

In FIG. 2 the valve construction is shown to include a main valve body 20 with a tubular adapter section having an internally tapered wall surface 21 to grippingly receive the tapered adapter tip of the metering syringe. Ears 22 and 23 can engage an internally threaded collar 24 of the metering syringe.

The valve main body portion has an inlet port shown in dotted line at 25. This inlet port is bridged by a pressure post 26. An inlet adapter 27 is sealingly attached to the main body portion of the valve adjacent its inlet port. This inlet adapter includes a passage 28 and an annular valve seat 29. An imperforate rubber disk shaped inlet valve member 30 is lightly biased against valve seat 29 by pressure post 26. To provide free flexure of rubber disk 30 without unnecessarily binding against edge surfaces of the inlet adapter a series of guide ribs 31 are provided.

The valves main body portion has an outlet port 32 surrounded by an annular valve seat 33. An outlet adapter 34 has a passage 35 shown in dotted line. Spanning passage 35 is an outlet pressure post 36. Outlet adapter 34 is sealingly attached to the main body portion and pressure post 36 heavily biases an imperforate rubber disk valve 37 against the main body's annular valve seat 33. A series of spaced ribs 38 on the outlet adapter provide for free flexure of the rubber disk 37 of the outlet check valve.

The internally threaded collar 9 is shown in more detail in FIG. 2. This collar is assembled to the outlet adapter by forcing the collar over a snap rib 40 about which collar 9 is free to rotate.

If desired, a filter 41 can be included in a passage of the outlet or inlet of the adapter. This could be used to filter any particulate matter that may be in the reservoir containter or flexible tube leading to the valve.

The inlet rubber disk 30 is biased in its normally closed position with a much lighter pressure than the outlet rubber disk 37. Outlet rubber disk 37 could be adjusted to withstand head pressures equivalent of 10 to 100 inches of water prior to opening, while inlet valve disk member could be adjusted to withstand 0.1 to 10 inches of water head prior to opening. It has been found that the check valve of this invention works very well when the inlet disk valve has a pressure post biasing valve 30 to withstand approximately 48 inches of water head prior to opening, and the outlet disk valve has its pressure post biasing it to withstand approximately 2 inches of water head prior to opening.

The two check valves have one heavily biased imperforate disk and one lightly biased imperforate disk. Preferably the outlet disk is the one heavily biased.

The check valve structure of this invention can be made of a suitable rigid thermoplastic material, and the resilient disk valve members are preferably of a stamped rubber sheet material. Because of their simplicity in construction, the flexible disk valves are preferred to spring and ball check valves because the flexible disk valves have less tendency to clog and malfunction.

In the above description, a specific example has been used to describe the invention. It is understood that those skilled in the art can make certain modifications to this example without departing from the spirit and scope of this invention.

We claim:

1. A pumping system for medical fluids with a hypodermic syringe means connected to inlet and outlet check valves, wherein the improvement comprises: a valved body with an inlet passage from which pumped fluid is supplied, a syringe connecting passage, and an outlet passage, said passages being in fluid flow communication within said valved body; an inlet valve seat in the inlet passage facing downstream of inlet fluid flow; an outlet valve seat in the outlet passage facing downstream of outlet fluid flow; a flexible imperforate disk valve member fitted against each of the inlet and outlet valve seats; a pair of upstream facing posts internal of the valve body and connected to the valve body for respectively urging each disk valve member against its respective valve seat; one of said posts biasing its valve member so as to require a substantially greater opening pressure in the range equivalent to a water head of 10 to 100 inches, while the other post is positioned to require the other disk valve to open at a pressure in the range equivalent to a water head of 0.1 to 10 inches; and a flexible conduit connected to the inlet passage and which conduit is adapted to attach to a medical liquid source, whereby fluid can flow from a fluid supply source through the inlet passage into the syringe on an intake stroke of the syringe and be pumped out through the outlet passage while fluid flow out through the inlet passage is blocked.

2. A pumping system as set forth in claim 1, wherein there is a filter in one of the passages.

3. A pumping system as set forth in claim 1, wherein the inlet valve is more heavily biased than the outlet valve.

4. A pumping system as set forth in claim 1, wherein the outlet valve is more heavily biased than the inlet valve.

5. A pumping system as set forth in claim 1, wherein the body includes a main valve body with a tubular adapter section having an internally tapered wall for receiving a metering syringe or the like, and this main body includes a post; and a separately formed inlet adapter containing one of said valve seats, and said inlet adapter is secured to the main body portion of the valve.

6. A pumping system as set forth in claim 5, wherein the main body portion has said outlet valve seat against which fits one of said disk valves; and a separately formed outlet adapter with one of said posts secured to the main body portion to urge the disk valve into a closed position.

7. A pumping system as set forth in claim 1, wherein the valve body includes a main body portion with an inlet port; a tubular inlet adapter with an inlet passage surrounded by said inlet valve seat and containing said flexible inlet disk valve, said tubular inlet adapter which carries the inlet valve seat being sealingly attached to the main body member about its inlet port; said main body portion having an outlet port surrounded by said outlet valve seat; and a tubular outlet adapter containing said outlet passage, said tubular outlet adapter being sealingly attached to the main body portion and containing said flexible outlet disk valve; and said posts bridging respectively the inlet and outlet passages of the valve and urging the flexible inlet and outlet disks into engagement with their respective valve seats.

* * * * *